United States Patent
Fuchs

(10) Patent No.: US 6,595,389 B2
(45) Date of Patent: Jul. 22, 2003

(54) DEVICE FOR DETECTING THE OPERATION OF A DISPENSER AND THE DISPENSER

(75) Inventor: Karl-Heinz Fuchs, Radolfzell (DE)

(73) Assignee: Ing. Erich Pfeiffer GmbH, Radolfzell (DE)

(*) Notice: Subject to any disclaimer, the term of this patent is extended or adjusted under 35 U.S.C. 154(b) by 0 days.

(21) Appl. No.: 10/021,632

(22) Filed: Dec. 12, 2001

(65) Prior Publication Data

US 2002/0079326 A1 Jun. 27, 2002

(30) Foreign Application Priority Data

Dec. 23, 2000 (DE) .......................... 100 65 160

(51) Int. Cl.⁷ ................................. B67D 5/22
(52) U.S. Cl. .................. 222/38; 222/333; 222/644
(58) Field of Search .................. 222/38, 39, 63, 222/333, 642, 644

(56) References Cited

U.S. PATENT DOCUMENTS

| 4,350,265 | A | * | 9/1982 | Griffiths et al. ............... 222/38 |
| 5,020,527 | A |   | 6/1991 | Dessertine |
| 5,544,647 | A |   | 8/1996 | Jewett et al. |
| 5,809,997 | A |   | 9/1998 | Wolf |
| 5,823,390 | A | * | 10/1998 | Muderlak et al. ............. 222/38 |
| 6,182,655 | B1 |  | 2/2001 | Keller et al. |
| 6,202,642 | B1 |  | 3/2001 | McKinnon et al. |
| 6,249,717 | B1 | * | 6/2001 | Nicholson et al. ............ 222/38 |
| 6,267,297 | B1 | * | 7/2001 | Contadini et al. .......... 222/646 |

FOREIGN PATENT DOCUMENTS

| DE | 33 02 160 | 7/1984 |
| DE | 44 38 375 | 5/1996 |
| EP | 0 480 488 | 7/1991 |
| FR | 2 611 671 | 9/1988 |
| GB | 2 268 161 | 6/1993 |

* cited by examiner

Primary Examiner—Gene Mancene
Assistant Examiner—Melvin A Cartagena
(74) Attorney, Agent, or Firm—Quarles & Brady LLP

(57) ABSTRACT

A device for detecting the operation of a dispenser (11) includes a medium container (12) for storing a dischargeable medium, a discharge mechanism (13) operated by a relative movement between an operating element (14) and the medium container, the operating element (14) containing a detecting device (20) for detecting operations which have taken place and for generating an electric counting signal in response thereto, the operating element (14) also containing a display element (22) for displaying a numerical value determined in the counting mechanism (21) as a function of the number of counting signals which have occurred and the display element (22) only being activated for a period of time.

20 Claims, 1 Drawing Sheet

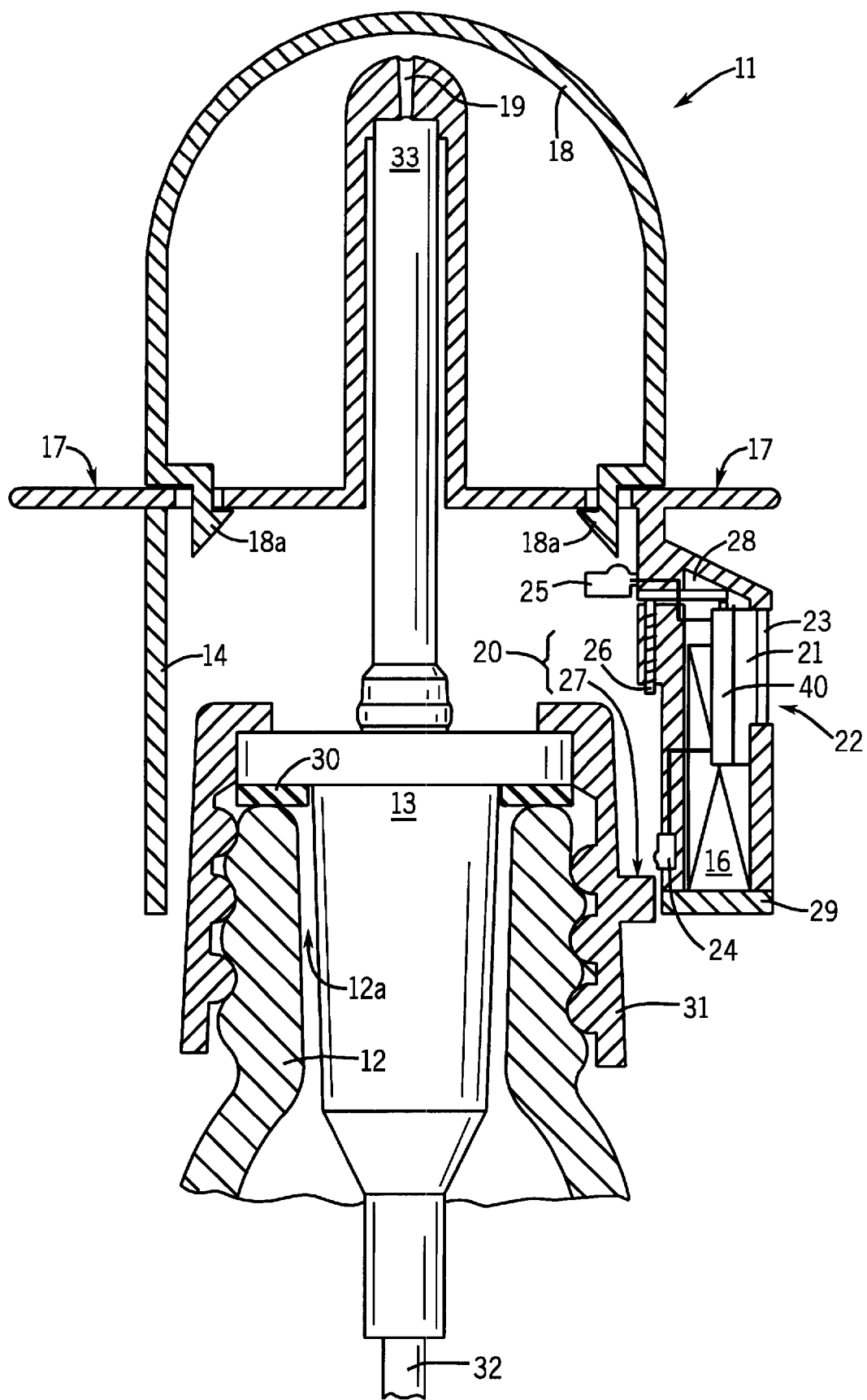

DEVICE FOR DETECTING THE OPERATION OF A DISPENSER AND THE DISPENSER

TECHNICAL FIELD

The invention relates to a device for detecting the operation or actuation of a dispenser, particularly a dispenser for liquid of solid media, preferably containing at least one pharmaceutical substance, as well as a device for discharging such media.

BACKGROUND OF THE INVENTION

The problem of the invention is to firstly simplify the detection of operations or actuations using a smaller number of precision components and on the other only to detect complete actuations or operations of the operating or actuating element. In addition, there must also be a greater security against manipulations and a better representation of large numbers.

In addition, with a counting wheel or other mechanical means, it is difficult to represent two or three-place numbers, because the available path between two scale dividers is extremely small.

The problem of the invention is to firstly simplify the detection of operations or actuations using a smaller number of precision components and on the other only to detect complete actuations or operations of the operating or actuating element. In addition, there must also be a greater security against manipulations and a better representability of large numbers.

DISCLOSURE OF THE INVENTION

A device according to the invention for detecting the operations of a dispenser is more particularly used for detecting the operation of a dispenser for solid or liquid media, preferably containing at least one pharmaceutical substance (e.g. opiates, calcitonin, oxitocin and adjuvants). The medium is stored in a medium container. On the medium container is provided a discharge means and its operation serves to discharge the medium. The operation of the discharge means takes place through a relative movement between an operating element and the medium container. According to the invention in the operating element is located a detecting device, e.g. a sensor, for detecting operations which have taken place of the operating element. The detecting device generates a counting signal, which serves to detect operations which have taken place.

According to a preferred development of the invention the electrical counting signal is processed in an electrical counting mechanism, which is preferably also located in the operating element.

For displaying the numeral value determined in the counting mechanism as a function of the number of counting signals which have occurred, a display element located in the operating element is used, more particularly in the form of an electrooptical display element or a one or a multi-place eight segment display. One example of such an electrooptical display element is a LCD display. It can also be a corresponding, small screen, e.g. a plasma screen. Such electrooptical display elements have the advantage of permitting an almost random information representation. Not only the number of the still available or the already performed operations can be given in the form of a numerical value, but also other information can be displayed, e.g. the number of operations per unit of time or roughly how long has elapsed since the last operation or how much time should elapse as a minimum up to the next operation. This information can not only be displayed as numerical values, but also in pictogram-like manner or using other symbols. The possibility and the number of displays increases with an increase in size of the display element. According to the invention the display element is located in the operating element and to the extent that the latter is linearly constructed in the vertical direction, but curved in the transverse direction thereto, there can also be a corresponding curvature of the display element.

A particularly advantageous development is obtained if the display element and electric counting mechanism are constructed as a continuous, one-piece component. This component consequently not only contains the control of the display and the physically constructed display element, but also the electric counting mechanism, i.e. the evaluation logic for the transmitting counting signals. The continuous component is in particular the LCD display control unit.

A device for discharging in particular solid or liquid media, preferably containing a pharmaceutical substance in accordance with the present invention and e.g. a dispenser, has a container for storing dischargeable medium. An operating element acts in such a way on a discharge means that through an operation of the operating element medium is discharged from the medium container. According to the invention the operating element contains an electrooptical display element.

According to a preferred development of the invention the display element is in the form of a LCD display. According to a further development of the invention the display element is connected to an evaluating unit or is constructed as part of an evaluating unit, in which are processed the signals of a sensor and where the display determines information as a function of sensor signals. It is also advantageous if the operating element contains an electric energy storage means for the energy supply of the display element of the evaluating unit.

According to an advantageous development of the device according to the invention the display element is only activated for a given display period, which is e.g. predetermined or is determined as a function of the given situation. This display duration limitation mainly serves to limit the energy consumption of the display element and consequently increases the service life of the device. According to a further development of the invention the display duration is preferably limited to a predetermined time after the last signal modifying the displayed information. A display-modifying signal is e.g. a signal which is detected in the sensor and which serves to modify the numerical value and consequently also change the information displayed as a function of the numerical value.

It is possible for the display element to be transferred from an unactivated non-display state into a state where there is a display of information, in that there is a slight operation of the operating element, but which does not lead to a discharge of medium. It is common to many dispensers that it is necessary to overcome a certain idle path of the actuating means before a discharge process is initiated or starts. This idle path can be used in that during the same a signal is generated, e.g. by contacting or interrupting contacting of an electric switch connected to the evaluating unit.

Alternatively or additionally a suitable detecting device, e.g. a further switch, can detect whether or not a protective cap has been fitted in order to protect the dispenser when the latter is not in use. By means of said detecting device it is possible to detect both the removal and the fitting of the protective cap and alternatively the placing of the protective cap on the dispenser can lead to a deactivation of the display element and/or the removal of the cap from the dispenser can lead to an activation of the display element.

According to a preferred development of the invention the actuating element is constructed as a one-piece component incorporating the dispenser discharge opening. The component is in particular simultaneously constructed as an applicator to be fitted to the administration location and in particular in the form of a nasal or buccal applicator.

These and other features can be gathered from the claims, description and drawing and the individual features, both singly and in the form of subcombinations, can be implemented in an embodiment of the invention and in other fields and can represent advantageous, independently protectable constructions for which protection is claimed here.

BRIEF DESCRIPTION OF THE DRAWING

These and further developments of the invention can be gathered from the embodiment shown in the single drawing, which is in the form of a part sectional, diagrammatic representation of devices according to the invention.

DETAILED DESCRIPTION OF THE PREFERRED EMBODIMENT

The drawing shows a dispenser 11 in an only partly represented medium container 12, which can store a medium to be discharged. The medium to be discharged can be in the form of liquids, which can have different viscosities and which can range from highly viscous to very thin liquids, such as alcohol-based solutions. In addition, the media to be stored usually contain a pharmaceutical substance.

The discharge means 13 is inserted in the medium container opening 12a. The discharge means 13, which in the represented embodiment is a plunger pump, is sealingly mounted by means of the sealing ring 30 on the opening 12a (e.g. an atomizer nozzle) and is held firmly on the medium container 12 by the fixing screw 31. In the manner shown in the embodiment, the discharge means 13 can e.g. be a plunger pump, which with a suction hose 32 sucks medium from the lowest point of the medium container 12 and delivers the medium through the riser 33 to the discharge opening.

The discharge means 13 is operated by operating the operating element 14. For this purpose the operating element 14 carries contact surfaces 17, where the user can apply his fingers and a discharge stroke of the plunger pump can be brought about by pressing down the operating element 14 towards the medium container 12. The thumb can e.g. act on the underside of the medium container for producing the corresponding opposing force. During each discharge stroke there is a discharge of medium through the discharge opening 19. For this purpose the operating element 14 is constructed in such a way that it acts by means of the riser 33 on the plunger of the plunger pump serving as the discharge means 13. The operating element can be displaced by the plunger height of lift relative to the discharge means and therefore relative to the medium container. In order to bring about a reliable relative position between the operating element 14 and medium container 12, it is also possible to provide a radial guide between the fixing screw 31 or medium container 12 and the operating element 14. This can in particular be created in that the fixing screw 31 has a non-circular outer contour and the shape of the operating element 14 is adapted thereto. However, it is also possible to provide guide rails, guide grooves and guide surfaces. It is also possible for the fixing screw 31 to be part of a housing surrounding the medium container 12 or for it to be shaped as part thereof.

To protect the discharge opening 19 against dirtying when the dispenser 11 is not in use and also to secure the dispenser against undesired operation during non-use, a protective cap 18 can be placed on the operating element 14 and covers the discharge opening 19.

The operating element has a detecting device 20, which is used to indicate operations of the operating element 14 which have taken place. The detecting device 20 comprises the switching element 26, which is located on the side of the operating element 4 and the switching surface 27 formed on the fixing screw side. As soon as the switching element 26 engages with the switching surface 27, a counting signal is generated, which is transmitted to the counting mechanism 21. As a function of the number of detected counting signals, a numerical value is determined at the counting mechanism 21. In the simplest case the numerical value can be the total number of operations of the operating element. However, it can also be the number of operations which have taken place within a given time, e.g. within an hour or a day. Alternatively or additionally the numerical value can be the number of still remaining operations leading to a discharge of medium. This is e.g. of interest if the medium container contains a precisely dosed medium quantity and the user wishes to know how often a dose can be administered before the container is completely emptied. The detecting device 20 with its switching element 26 and switching surface 27 consequently forms a sensor for the performance of a complete operation of the operating element 14.

On the operating element 14 is also provided an idle path switch 24, which detects an operation of the operating element 14 in the vicinity of the idle path, i.e. without discharging medium. This idle path switch 24, which can be in the form of a push-button switch, transmits a corresponding switching signal at the start of any operation of the operating element 14. As a result of a switching signal of the idle path switch 24 the display element 22 can be controlled and in particular switched on.

In addition, a protective cap switch 25, which can also be a push-button switch, is positioned outside the movement path of the container 12 and the fixing screw 31 on the operating element 14. It is possible to detect by means of the protective cap switch 25, it is possible to detect whether the protective cap 18 is placed on the discharge means 11, particularly on the operating element 14. For operating the protective cap switch 25 can in particular be used a latch 18a of the protective cap 18 projecting into the interior of the operating element 14 and which serves to maintain the cap 18 on the element 14. The switching state of the protective cap switch then represents the two states "protective cap fitted" and "protective cap not fitted". A corresponding signal is supplied to the display element 22.

The display element 22 can in particular comprise a LCD display 23, a small colour screen and control electronics, which can also be called an evaluating unit 40. The control electronics and the counting mechanism 21 are preferably constructed as a common electronic component. The LCD display 23 can also be directly fitted to said electronic component. The energy supply of the display element and the counting mechanism 21 is provided through the energy storage means 16, e.g. a battery or button cell. For receiving the counting mechanism 21, the display control, including evaluating unit 40, and the display element 22, a chamber 28 is provided on the operating element 14 and is closed by means of the lid 29. The display element 22, e.g. the LCD screen, forms the corresponding termination of an opening in the chamber 28 towards the user or observer. The lid 29 can be placed both detachably, non-detachably and in sealing manner or in non-hermetically terminating manner on the operating element 14.

The operation of the device according to the invention will now be described. If the protective cap 18 is removed from the operating element 14, there is change to the switching state of the protective cap switch 25. The change to the switching state of the protective cap switch 25 is detected as a signal in the evaluating unit 40 and counting mechanism 21 and the display element 22 is activated. On the LCD screen 23 is then displayed a counting signal, e.g. the number of operations to the operating element 14 which have already taken place. If there is no operation of the operating element 14, then the display is switched off again for specific, predetermined time, e.g. approximately 30 seconds to 1 minute.

A renewed switching on of the display can take place in that there is a slight operation of the operating element 14 and consequently a switching of the idle path switch 24. This also leads to an activation of the screen, at least for a given time period. On operating the operating element 14, which only activates the idle path switch 24, no medium is discharged from the discharge opening 19. If the user operates the operating element 14, when medium is discharged from the discharge opening 19 and for which purpose the operating element constructed in this area as an applicator is introduced with the discharge opening 19 at the application location, e.g. into the nose or mouth, the operating element 14 is moved relative to the fixing screw 31 until the switching element 26 engages with the switching surface 27. As a result an electric counting signal is generated and supplied to the counting mechanism 21. Due to the counting signal the counting mechanism now knows that a further operation of the dispenser 11 has taken place. A corresponding change as a result of the determined count value, which has now changed, is henceforth displayed. The display is extinguished either at the end of a preset time, e.g. a time interval of 30 seconds to 1 minute, or if the protective cap 18 is again placed on the operating element 14 and consequently there is again a change to the switching state of the protective cap switch 25. However, there can also be a certain overtravel following the fitting of the protective cap 18 and as a result the display of the LCD display element 23 can appear for a preset time following the fitting of the cap 18. It can e.g. be a time period of less than 1 minute, e.g. 10 to 30 seconds. The individual time intervals for switching off (transition of the display to the "non-activatable" state) can also take place in parallel and it is possible for the actual switching off to take place with the termination of the last finishing interval and for switching off to take place with the end of the first finishing interval.

What is claimed is:

1. Device for detecting the operation of a dispenser, comprising a medium container storing dischargeable medium, having a discharge means for discharging the medium from the container, the discharge means being operated by a relative movement between an operating element and the medium container, wherein the operating element contains a detecting device for detecting operations which have taken place and which generates an electric counting signal for detecting operations which have taken place; the operating element containing a display element for displaying a numerical value determined in the counting mechanism as a function of the number of counting signals which have occurred; and the display element being only activated for a given period of time.

2. Device according to claim 1, wherein the electric counting mechanism is located in the operating element.

3. Device according to claim 1, wherein the display element in an electrooptical display element.

4. Device according to claim 1, wherein the display element is constructed as a LCD display.

5. Device according to claim 4, wherein the counting mechanism is integrated into the control unit of the LCD display.

6. Device according to claim 1, wherein the display element and electric counting mechanism are constructed as a continuous component.

7. Device according to claim 1, wherein the display period is limited to a given time interval after the last signal modifying the displayed information.

8. Device according to claim 1, wherein the activation of the display element takes place through an operation of the operating element not leading to a medium discharge.

9. Device according to claim 1, wherein the operating element is constructed as a one-piece component incorporating the discharge opening of the dispenser.

10. Device according to claim 9, wherein the component is constructed as an applicator to be fitted at an administration point.

11. Device according to claim 1, wherein the dispenser dispenses a medium containing at least one pharmaceutical substance.

12. Device according to claim 1, wherein the device dispenses a medium containing at least one pharmaceutical substance.

13. Device for detecting the operation of a dispenser, comprising a medium container storing a dischargeable medium, having a discharge means for discharging the medium from the container, the discharge means being operated by a relative movement between an operating element and the medium container, wherein the operating element contains a detecting device for detecting operations which have taken place and which generates an electric counting signal for detecting operations which have taken place; the electric counting mechanism being located in the operating element and a protective cap being provided for protecting the dispenser during non-use periods, in which the placing of the protective cap on the dispenser brings about a deactivation of a display element and the removal of the protective cap from the dispenser brings about an activation of the display element.

14. Device according to claim 13, wherein the display element is constructed as a LCD display.

15. Device for discharge of media, having a container for storing dischargeable medium, an operating element for bringing about a discharge of medium from the medium container by a discharge means, an electrooptical display element being located in the operating element, the operating element containing an electric energy storage means for the energy supply of the display element, and the display element being only activated for a given period of time.

16. Device according to claim 15, wherein the display element has an evaluating unit, to which are supplied the signals of a sensor and in which the display of the display element is determined as a function of the sensor signals.

17. Device according claim 15, wherein the operating element contains an electric energy storage means for the energy supply of the display element and optionally the evaluating unit.

18. Device according to claim 15, wherein the display period is limited to a given time interval after the last signal modifying the displayed information.

19. Device according to claim 15, wherein the activation of the display element takes place through an operation of the operating element not leading to a medium discharge.

20. Device for discharge of media, having a container for storing a dischargeable medium, an operating element for bringing about a discharge of medium from the medium container by a discharge means, an electrooptical display element being located in the operating element, a protective cap being provided for protecting the dispenser during non-use periods, in which the placing of the protective cap on the dispenser brings about a deactivation of the display element and the removal of the protective cap from the dispenser brings about an activation of the display element.

* * * * *

UNITED STATES PATENT AND TRADEMARK OFFICE
CERTIFICATE OF CORRECTION

PATENT NO. : 6,595,389 B2
DATED : July 22, 2003
INVENTOR(S) : Karl-Heinz Fuchs

It is certified that error appears in the above-identified patent and that said Letters Patent is hereby corrected as shown below:

<u>Column 1,</u>
Line 31, "representability" should be -- representation --.

Signed and Sealed this

Twentieth Day of April, 2004

JON W. DUDAS
*Acting Director of the United States Patent and Trademark Office*